US00PP36341P2

(12) United States Plant Patent
Volz

(10) Patent No.: US PP36,341 P2
(45) Date of Patent: Dec. 31, 2024

(54) APPLE TREE NAMED 'PremA021'

(50) Latin Name: *Malus domestica*
Varietal Denomination: PremA021

(71) Applicant: Prevar Limited, Hastings (NZ)

(72) Inventor: Richard Volz, Auckland (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 18/668,017

(22) Filed: May 17, 2024

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
CPC ..... A01H 5/08; A01H 5/00; A01H 6/7418; A01H 6/74
See application file for complete search history.

(56) References Cited

U.S. PATENT DOCUMENTS

PP28,546 P3 * 10/2017 Howell ..... A01H 5/08 Plt./161

* cited by examiner

*Primary Examiner* — June Hwu
(74) *Attorney, Agent, or Firm* — Michelle Bos Legal LLC

(57) ABSTRACT

A new and distinct apple tree named 'PremA021' notable for its attractive fruit. The fruit flesh of 'PremA021' is yellow-orange and red-purple.

5 Drawing Sheets

Latin name: *Malus domestica.*
Variety denomination: PremA021.

BACKGROUND OF THE VARIETY

The new apple tree 'PremA021' was created in the course of a planned breeding program carried out at Havelock North, New Zealand. 'PremA021' originated from a controlled cross of 'PremA153' (seed parent, U.S. Plant Pat. No. 21,936) and 'A195R30T051' (pollen parent, not patented) performed at Havelock North, New Zealand in 2004. 'PremA021' was selected from a population of seedlings derived from the parents, and was singled out for further observation because of its fruit, which has attractive bicolored flesh and appealing flavor. The variety was first asexually propagated by grafting onto 'M9' rootstock (not patented) at Havelock North, New Zealand in 2011. 'PremA021' trees have been observed over a number of asexually propagated generations, and have been found to remain true to type.

BRIEF SUMMARY OF THE INVENTION

'PremA021' is distinguished from parent variety 'PremA153' primarily by its fruit. 'PremA021' has red-purple and yellow-orange fruit flesh, while the fruit flesh of 'PremA153' is white. The fruit of 'PremA021' is distinguished from that of parent variety 'A195R30T051' by its larger size, later harvest maturity, and distinct russeting pattern. 'Howell TC3' (U.S. Plant Pat. No. 28,546), sold commercially under the Lucy Glo™ trademark, is the most similar commercial variety. Comparison of 'PremA021' to 'PremA153' and to 'Howell TC3' are set forth in Table 1 below, and a comparison of 'PremA021' to 'A195R30T051' is set forth in Table 2 below.

TABLE 1

Comparison of 'PremA021' to 'PremA153' and 'Howell TC3'

| Characteristic | 'PremA021' | 'PremA153' | 'Howell TC3' |
|---|---|---|---|
| Fruit Flesh Color | Red-purple 58B and yellow-orange 19C | White 155A | Red 50B and white 155B |

TABLE 2

Comparison of 'PremA021' to 'A195R30T051'

| Characteristic | 'PremA021' | 'A195R30T051' |
|---|---|---|
| Fruit size | Larger, average 210 g | Smaller, average 190 g |
| Fruit russeting pattern | Around stem | All over |
| Harvest maturity | Early October | About two weeks before 'PremA021' |

BRIEF DESCRIPTION OF THE PHOTOGRAPHS

The attached photographs of trees and fruit were taken at Wapato, Washington during the 2023 growing season; blossom photographs were taken in 2024. The trees depicted were planted in 2020 and grown on 'M9' rootstock (not patented).

Figure 1:
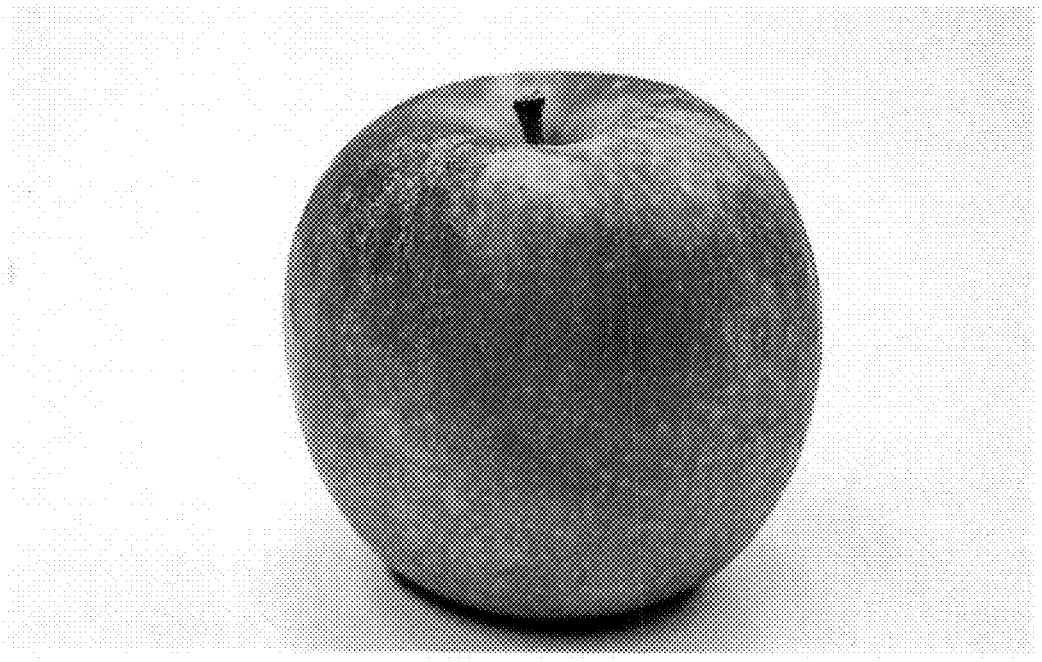
Figure 2:
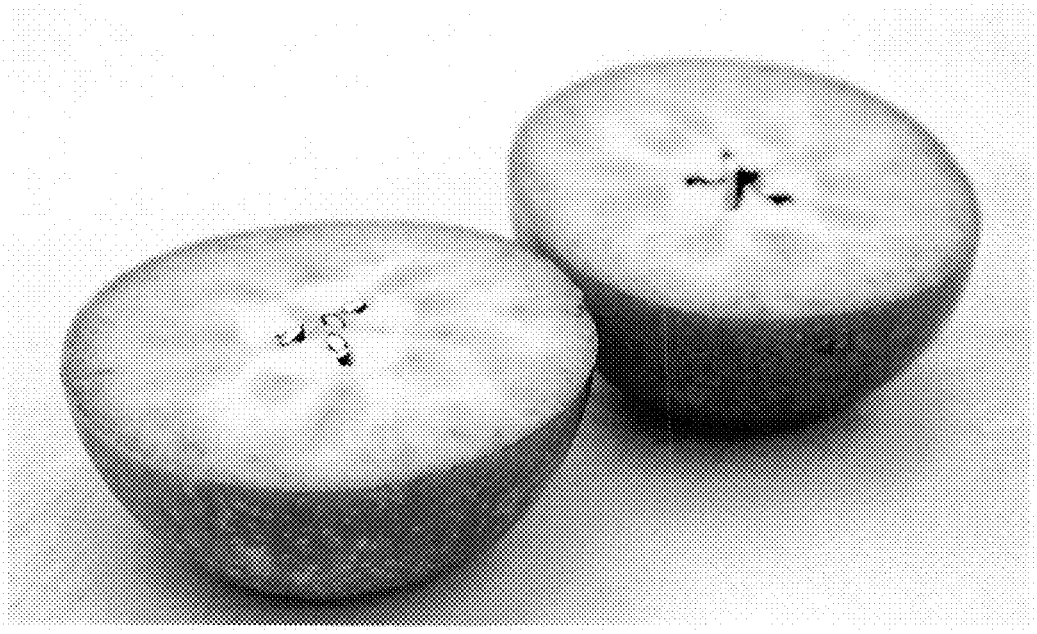
Figure 3:
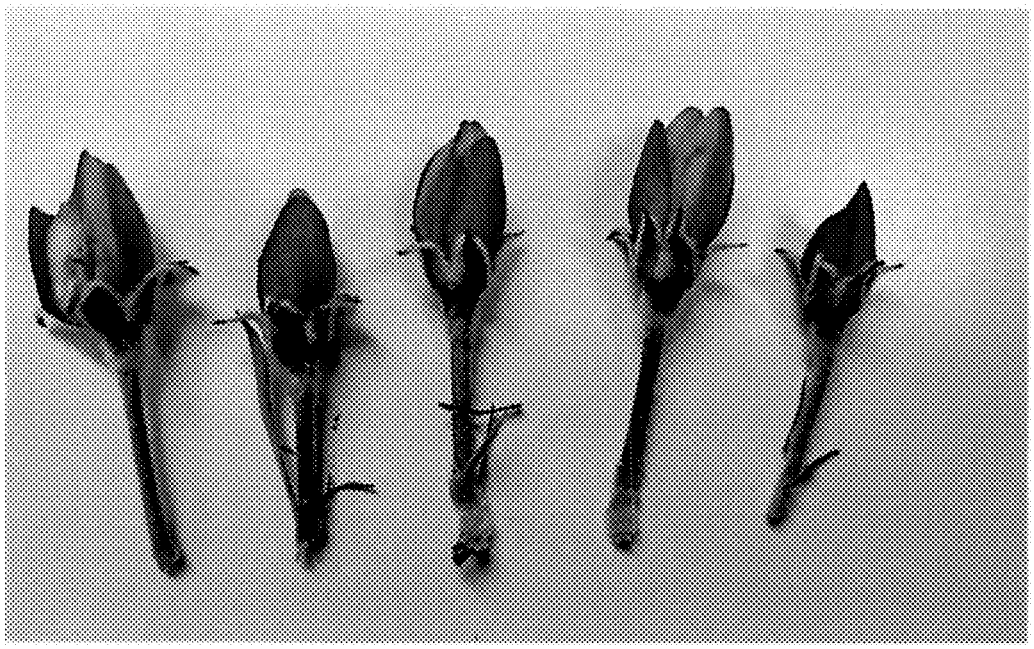
Figure 4:
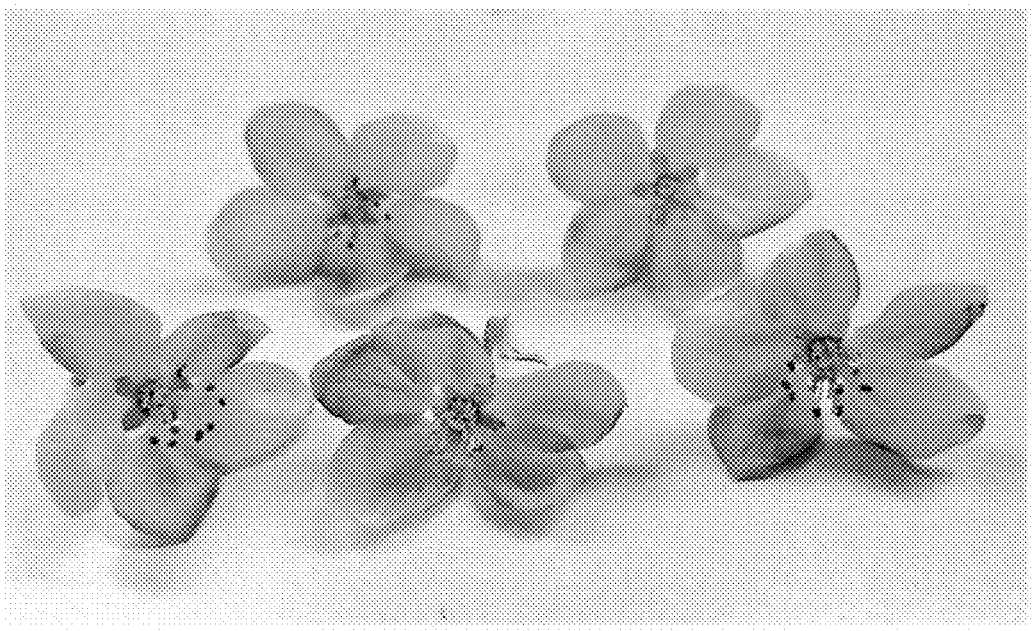
Figure 5:
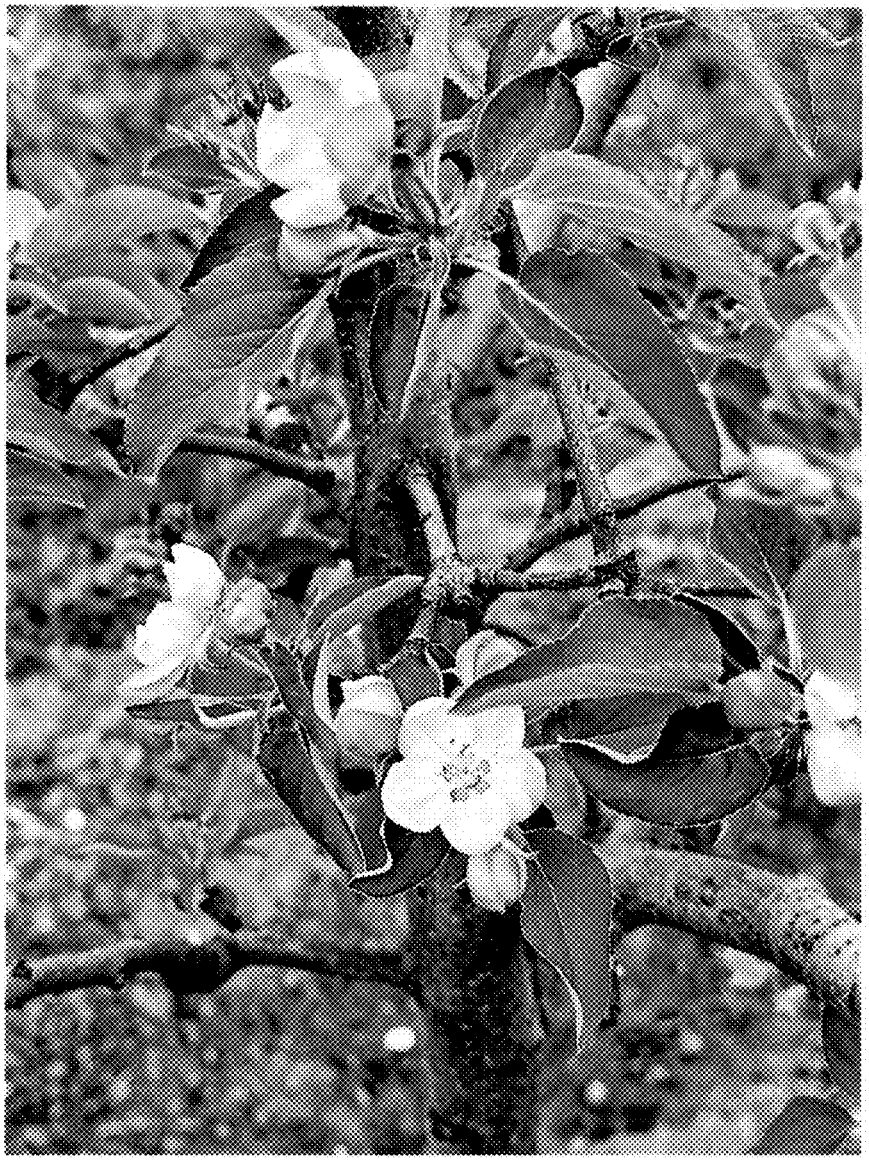
Figure 6:
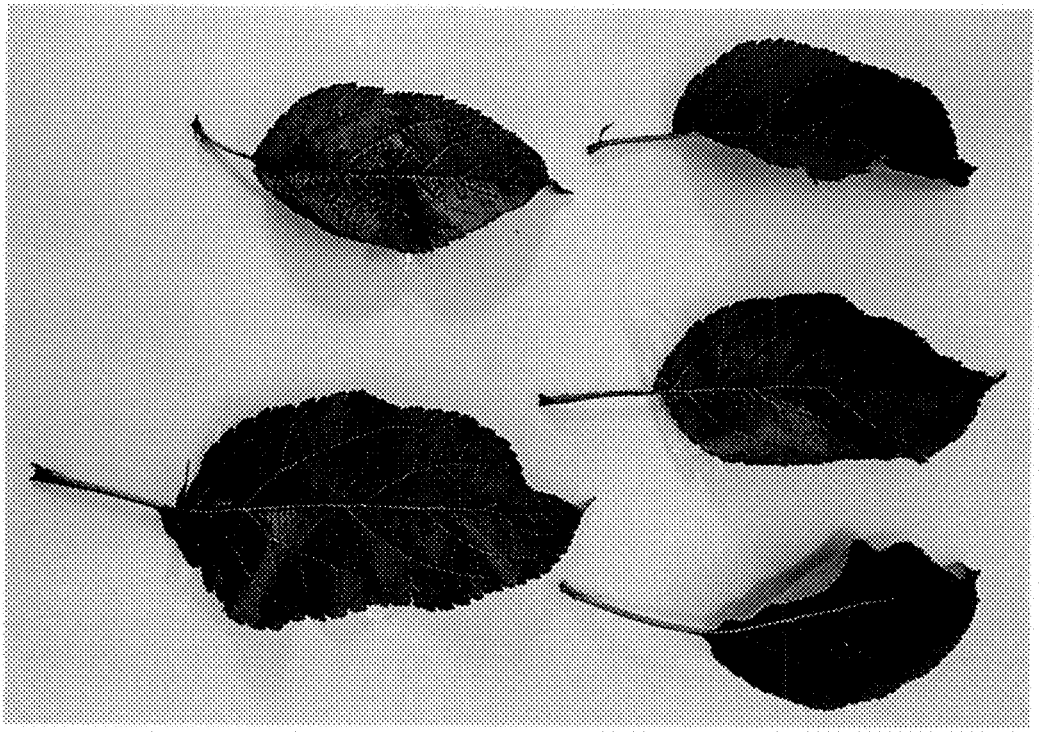
Figure 7:
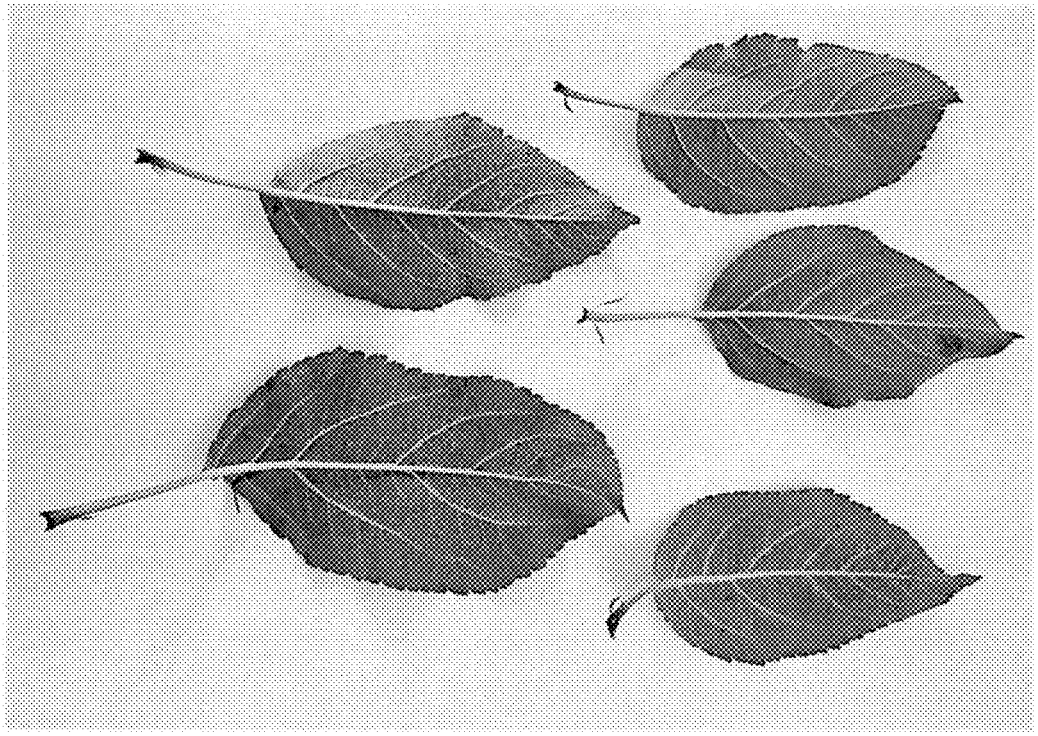
Figure 8:
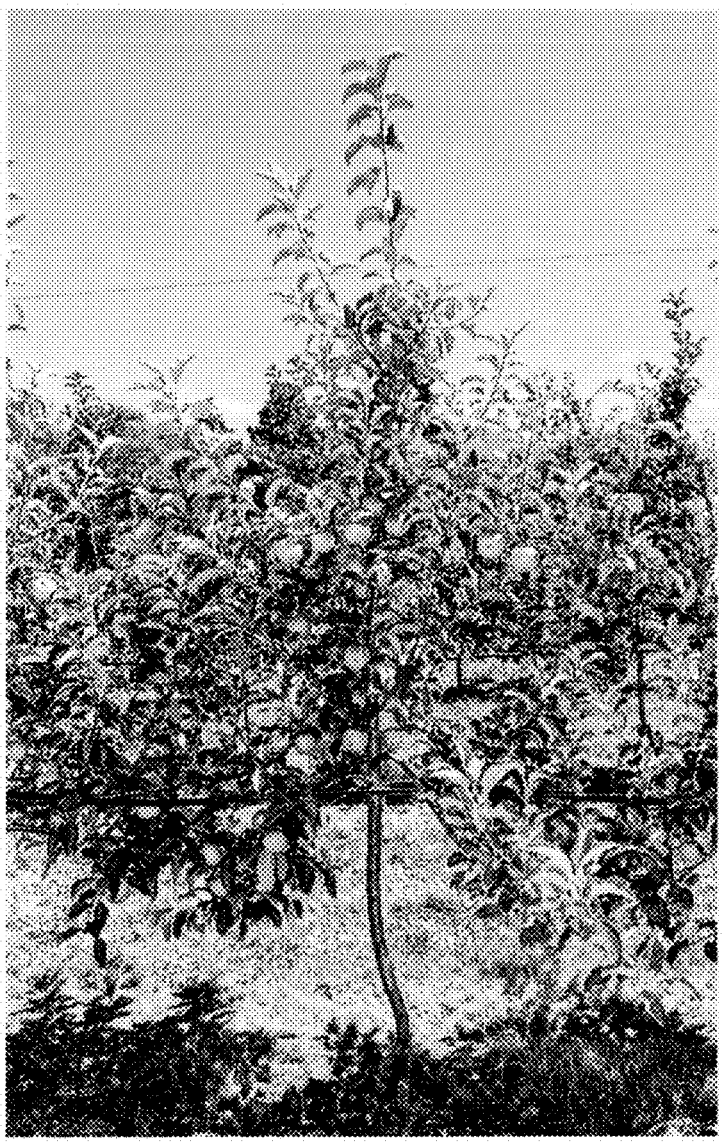

FIG. 1 shows the fruit of a 'PremA021' apple tree;
FIG. 2 shows a sectioned fruit of a 'PremA021' apple tree;
FIG. 3 shows the flower buds of a 'PremA021' apple tree;
FIG. 4 shows the flowers of a 'PremA021' apple tree;
FIG. 5 shows the trunk, leaves and flowers of a 'PremA021' apple tree;
FIG. 6 shows the upper surface of leaves of a 'PremA021' apple tree;
FIG. 7 shows the lower surface of leaves of a 'PremA021' apple tree; and,
FIG. 8 shows a 'PremA021' apple tree and its fruit.

DETAILED BOTANICAL DESCRIPTION OF THE VARIETY

The following-detailed botanical description is based on trees and fruit observed at Wapato, Washington during the 2023 growing season. Flower descriptions were recorded in 2024 at Wapato, Washington. The described trees were planted in 2020 and grown on 'M9' rootstock (not patented). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. All colors are described with reference to The R.H.S. Colour Chart, 6$^{th}$ ed. (Royal Horticultural Society, 2015).

Tree:
- *Vigor*.—Moderate.
- *Type*.—Ramified.
- *Habit*.—Spreading.
- *Height*.—1.5 m.
- *Spread*.—3.0 m.
- *Trunk diameter* (*at* 30 *cm above the graft*).—5 cm.
- *Bearing*.—On shoots and spurs.
- *Bark texture*.—Rough.
- *Bark color*.—Greyed-orange 166D.
- *Lenticel length*.—6 mm.
- *Lenticel width*.—2 mm.
- *Lenticel shape*.—Elliptic.
- *Lenticel color*.—White 155D.
- *Lenticel density*.—8 per cm$^2$.

Branch (fruiting branches located at around 1 m above the graft union):
- *Length*.—27 cm.
- *Diameter*.—7 mm.
- *Crotch angle*.—70°.
- *Bark color*.—Grey-orange 164A.
- *Branch lenticel length*.—2 mm.
- *Branch lenticel width*.—1 mm.
- *Branch lenticel shape*.—Elongated.
- *Branch lenticel color*.—White 155D.
- *Branch lenticel density*.—7 per cm$^2$.

One year old shoot:
- *Length*.—20 cm.
- *Diameter*.—4 mm.
- *Color*.—Greyed-orange 166B.
- *Pubescence*.—Present, moderate.
- *Internode length*.—3.5 cm.
- *Shoot lenticel length*.—1 mm.
- *Shoot lenticel width*.—0.5 mm.
- *Shoot lenticel shape*.—Elongated.
- *Shoot lenticel color*.—White 155A.
- *Shoot lenticel density*.—Dense.

Flower buds:
- *Stage described*.—Balloon.
- *Quantity per spur*.—*Average* 5.
- *Bud shape*.—Globose.
- *Apex shape*.—Rounded.
- *Length*.—12 mm.
- *Diameter*.—9 mm.
- *Color*.—Red-purple N57C.

Flowers:
- *Diameter of fully open flower*.—50 mm.
- *Depth of fully open flower*.—Shallow.
- *Relative position of petal margins*.—Overlapping.
- *Date of first bloom*.—Apr. 6, 2024.
- *Date of full bloom*.—Apr. 10, 2024.
- *Pollination requirement*.—Pollinator required.

Petals:
- *Number per flower*.—5.
- *Petal shape*.—Ovate.
- *Length*.—25 mm.
- *Width*.—20 mm.
- *Apex shape*.—Rounded.
- *Base shape*.—Rounded.
- *Margin*.—Entire.
- *Color of upper surface*.—White N155D with red-purple N74D veins and tips.
- *Color of lower surface*.—Red-purple N74D.

Pistils:
- *Quantity*.—4 to 5 per flower.
- *Length*.—10 mm.
- *Color*.—Yellow-green 144C.

Stigma:
- *Diameter*.—1 mm.
- *Color*.—Yellow-green 144C.

Style:
- *Length*.—8 mm.
- *Color*.—Yellow-green 144C.

Ovary:
- *Length*.—5 mm.
- *Color*.—Green 135C.

Stamens:
- *Quantity*.—15.
- *Length*.—6 mm.
- *Anther color*.—Yellow 8B.
- *Pollen*.—Abundant.
- *Pollen color*.—Yellow 8B.

Pedicel:
- *Length*.—20 mm.
- *Diameter*.—1 mm.
- *Color*.—Green 138C.

Sepals:
- *Quantity*.—5.
- *Color*.—Green 138C.
- *Length*.—7 mm.
- *Width*.—3 mm.
- *Shape*.—Acute triangular.
- *Apex shape*.—Acute.
- *Margin*.—Entire.

Leaves:
- *Shape*.—Ovate.
- *Length*.—7.5 cm.
- *Width*.—5 cm.
- *Blade margin*.—Serrate.
- *Apex*.—Acuminate.
- *Base shape*.—Rounded to cuneate.
- *Color of upper surface*.—Yellow-green 146B.
- *Color of lower surface*.—Yellow-green N148A.
- *Attitude in relation to shoot*.—Upward.

Petiole:
- *Length*.—25 mm.
- *Diameter*.—1 mm.
- *Color*.—Yellow-green 145C with greyed-purple 187D anthocyanin coloration at base.

*Stipules.*—1 or 2 present; length 5 mm; yellow-green N148A.

Fruit:

*Quantity per cluster.*—3 to 4 (after thinning).
*Diameter.*—75 mm.
*Height.*—65 mm.
*Weight.*—210 g.
*General shape in profile.*—Obloid.
*Position of maximum diameter.*—Near equator.
*Ribbing.*—Absent.
*Crowning at calyx end.*—Weakly present.
*Aperture of eye.*—Closed to partially open.
*Depth of eye basin.*—10 mm.
*Width of eye basin.*—25 mm.
*Length of sepal.*—5 mm.
*Bloom of skin.*—Absent.
*Greasiness of skin.*—Absent or weak.
*Background color of skin.*—Yellow 3D.
*Amount of over color.*—Large, 80%.
*Over color of skin.*—Red 43A.
*Intensity of over color.*—Moderate.
*Pattern of over color.*—Solid flush.
*Amount of russet around stalk cavity.*—Present, covering about 20%.
*Amount of russet on cheeks.*—Absent.
*Area of russet around eye basin.*—Absent.
*Length of stalk.*—25 mm.
*Thickness of stalk.*—2 mm.
*Depth of stalk cavity.*—12 mm.
*Width of stalk cavity.*—20 mm.
*Stalk color.*—Yellow-green 145C and red 47C.
*Firmness of flesh.*—Moderately firm.
*Flesh texture.*—Crisp.
*Juiciness.*—Juicy.
*Brix.*—11° Brix.
*Flesh color.*—Base color yellow-orange 19C more evident near core with mottled red-purple 58B coloration throughout flesh, more intense near surface.

Seeds:

*Quantity per fruit.*—7.
*Shape.*—Oval, symmetrical.
*Length.*—6 mm.
*Width.*—4 mm.
*Color.*—Greyed-orange 166B.
*Locules.*—Closed to slightly open.

Harvest:

*Time for harvest.*—Oct. 3, 2024, (Wapato, Washington).
*Number of picks.*—One.
*Storage characteristics.*—Stores well in regular air storage for up to 16 weeks.
*Market use.*—Fresh, cider.

I claim:

1. A new and distinct apple tree named 'PremA021', substantially as described and illustrated herein.

* * * * *